United States Patent [19]

Sanchez

[11] Patent Number: 5,405,609
[45] Date of Patent: Apr. 11, 1995

[54] THERAPEUTIC SHAMPOO COMPOSITION

[76] Inventor: Israel L. Sanchez, Calle 20 T-22, Urb. Las Vegas Catano, P.R. 00962

[21] Appl. No.: 104,760

[22] Filed: Aug. 12, 1993

[51] Int. Cl.⁶ .................... A61K 35/78; A61K 47/46
[52] U.S. Cl. .................... 424/195.1; 514/783; 514/852; 514/881; 514/863; 514/864
[58] Field of Search .............. 424/70, 195.1, 74; 514/880, 881, 863, 864, 852, 783

[56] References Cited

U.S. PATENT DOCUMENTS

| | | | |
|---|---|---|---|
| 112,632 | 3/1871 | Reybert | 424/74 |
| 915,781 | 3/1909 | Marshall | 424/74 |
| 4,292,971 | 10/1981 | Smit | 128/256 |
| 4,511,555 | 4/1965 | Faust | 424/74 |
| 4,822,604 | 4/1989 | Knoll et al. | 424/70 |
| 4,950,481 | 8/1990 | Kéri | 424/195.1 |
| 5,118,673 | 6/1992 | Carpenter | 514/54 |
| 5,152,990 | 10/1992 | Miyauchi | 424/400 |

FOREIGN PATENT DOCUMENTS 807106  2/1969  Canada .................. 424/70

*Primary Examiner*—Thurman K. Page
*Assistant Examiner*—Sally Gardner
*Attorney, Agent, or Firm*—Richard C. Litman

[57] ABSTRACT

A therapeutic composition for treatment of scalp disorders which comprises liquid castile soap, an aqueous extract from corncobs and aloe vera gel. The essential ingredients of the composition may be separately prepared and subsequently combined in relative proportionalities to produce a homogeneous liquid mixture having a consistency suitable for application as a shampoo to the hair and scalp. The shampoo composition can effectively eliminate dandruff in the hair, alleviate itching of the scalp, prevent hair loss and also accelerate hair growth.

6 Claims, No Drawings

THERAPEUTIC SHAMPOO COMPOSITION

BACKGROUND OF THE INVENTION

1. Field of the Invention

The present invention relates to a shampoo composition for the treatment of scalp disorders. More particularly, this invention pertains to a therapeutic shampoo composition which is effective in eliminating the generation of dandruff in hair and itching in the scalp, as well as in preventing hair loss and promoting the growth of hair.

2. Description of the Prior Art

Dandruff, seborrheic dermatitis and psoriasis are symptomatic disorders that show a predilection for the scalp. These particular scalp conditions are of unknown causes and are generally characterized by varying degrees of redness, scaling and oftentimes itching. It is widely believed that dandruff, for example, is associated with excess secretions of the sebaceous glands which become abnormally accelerated by bacterial infection of the scalp. For this reason, hair treatment compositions containing various bactericides have previously been used in the prior art for preventing dandruff. However, some bactericides are known to exhibit adverse side effects and, therefore, it is desirable to avoid their use for therapeutic purposes in most commercial hair formulations. It is also well known in the art that keratolytic agents are effective for alleviating the generation of dandruff and itching of the scalp. For instance, U.S. Pat. No. 4,822,604 to Knoll et al. discloses a detergent shampoo composition containing salicylic acid or a salicylate as the keratolytic agent for use in the local treatment of dandruff, seborrheic dermatitis and psoriasis. In addition, a shampoo formulation containing an oil extract of herbs for controlling dandruff is described in U.S. Pat. No. 4,511,555 to Faust.

Epilation and alopecia (i.e., the involuntary loss of hair and subsequent baldness) are other scalp affections which may arise from various causes. It is generally considered that epilation or baldness is related to abnormalities in the capillary vessels and epidermal cells due to influences of the endocrine and central nervous systems. In any case, hair follicles cannot complete their normal cycle in order to reach the hair generation or anagen state, and remain mostly unconverted from the telogen or resting phase of the hair cycle.

To prevent or alleviate hair loss and stimulate hair growth, various agents exhibiting pharmaceutical properties have been used in hair tonic compositions. Such pharmaceutical agents include a vitamin such as vitamin E, amino acids such as serine and methionine, anti-inflammatory agents, a vasodilator such as an acetycholine derivative, an estrogen such as estradiol, a stimulant such as cepharanthine, and keratolytics. Also, natural ingredients have been incorporated into hair tonics to allegedly promote the growth of human hair. Such naturally occurring components include mixtures of plant extracts such as castor oil, tincture of sage and oil of bergamot as disclosed in U.S. Pat. No. 112,632 to Reybert, and olive oil in admixture with the leaves of certain plants as described in Pat. No. 915,781 to Marshall. More recently, U.S. Pat. No. 5,152,990 to Miyauchi sets forth a hair grower containing components of citruses and an aloe extract.

The hair treatment compositions of the prior art claim to prevent or alleviate one or more of the various types of scalp pathologies mentioned above. However, at present there are no truly effective formulations available for substantially improving dandruff, itchiness and hair loss, as well as for accelerating hair generation and growth.

SUMMARY OF THE INVENTION

Accordingly, it is an object of the present invention to provide a therapeutic composition which is capable of effectively suppressing the generation of dandruff and itching of the scalp, and also preventing hair loss and stimulating the growth of hair.

It is among the further objects of the invention to provide a scalp treatment composition which is stable, simple to prepare and has a low probability of causing adverse side effects.

These and other objects are accomplished in accordance with the present invention which provides a therapeutic shampoo composition consisting essentially of about 45–55% by weight of liquid castile soap, about 25–30% by weight of a corncob extract and 20–25% by weight of aloe vera gel. The essential ingredients of the present composition may be separately prepared and subsequently combined in the designated proportionalities to produce a homogeneous liquid mixture having a consistency suitable for application as a shampoo to the hair and scalp. Regular use of the present shampoo composition over a period of several weeks results in a substantial elimination of dandruff, alleviation of itching of the scalp and also acceleration of hair growth.

The foregoing and other aspects, advantages and objects of the invention may be more fully appreciated by reference to the following detailed description.

DETAILED DESCRIPTION OF THE PREFERRED EMBODIMENTS

The castile soap component utilized in the compositions according to the present invention is a fine, hard, white, odorless soap which is conventionally made by saponification of olive oil with sodium hydroxide. The dry castile soap is first dissolved in sufficient water and the resulting soap solution is then boiled until a paste containing about 25–35% of the soap is formed. Generally, a solution consisting of about 20% by weight of the dissolved soap may be boiled for approximately 20 minutes at 200° F. in order to obtain a paste of the appropriate consistency. The paste is finally diluted with enough water to prepare an aqueous solution having a concentration of about 5–10% by weight of castile soap. Preferably, the shampoo compositions of the invention comprise about 50% of this aqueous castile soap solution. For purposes of the present invention, the aqueous medium preferably consists of spring water since it serves as an efficient solvent or carrier for the active ingredients. However, purified or deionized water in which the ions have been removed may also be a suitable carrier in the present compositions.

Another essential ingredient of the present compositions includes the liquid latex (exudate) or clear gel (mucilage) of the aloe vera plant. Aloe vera gel, the mucilaginous jelly from the parenchyma cells of the plant, is preferred and fresh gels of the aloe plant are most preferred. The gel from a suitable number of aloe vera plants may be removed by any convenient means such as by hand or roll pressing. Alternatively, the viscous extract from pulp of the aloe vera plant may also be used to form a gelatinous substance. In this particular embodiment, aloe vera leaves are ground and pressed into a pulpous mass which is then extracted by water with moderate heating until an aqueous aloe vera extract having the constituency of a gel is formed. For instance, a water-pulp admixture containing about 15% by weight of the aloe vera pulp can be heated for approximately 30 minutes at 200° F. to produce a concentrated extract. The resulting viscous extract contains about 20-25% of insoluble aloe vera gel, which preferably comprises about 22% of the present shampoo compositions.

The remaining component of the compositions of the present invention is an aqueous corncob extract. The woody cores of ears of Indian corn (Zea mays) in which the kernels have been removed are first dried under relatively moderate environmental conditions. The dried corncobs may be reduced by grounding to a suitable particulate substance and the ground corncobs are then extracted with spring water, for example. The mixture of corncobs and water are cooked for approximately 30 minutes at 200° F. until a relatively concentrated aqueous extract results. The resulting aqueous extract contains about 20% of the insoluble constituents of corncob, and the compositions of the present invention comprises, preferably, about 28% of this essential extract component.

The final preparation of the compositions of the present invention may be achieved economically and rapidly by simply combining the three essential components to produce a uniform liquid mixture. Preferably, the liquid castile soap, aloe vera gel and corncob extract in the designated proportions are intermixed by suitable agitation, as by a standard mixer. Alternatively, the corresponding soap paste and remaining components of the present composition can be mixed with a less than total quantity of water, and the resulting mixture diluted with the remaining amount of water while stirring to form the homogeneous liquid. The uniformity in consistency of the present preparations may be accelerated by subjecting the mixture of ingredients to heat, within the range of approximately 120° F. to 140° F., with attendant stirring. However, it should be understood that the mixed ingredients will present an homogeneous appearance with agitation under ambient conditions without the need for heating. The resulting compositions of the present invention are stable, homogenous solutions or suspensions that do not separate upon prolong storage.

In addition to the above named ingredients, other additives that may be incorporated into the present shampoo include, but not limited to, commonly used thickeners, fragrances, opacifiers, pearlescing agents, preservatives, sequestering agents, and the like. These cosmetic additives are usually present in weight percentages of 1% to 5% total and do not adversely affect the essential properties of the therapeutic compositions of the present invention. Suitable thickeners comprise cellulose derivatives such as methyl cellulose, hydroxyethylcellulose and carboxymethycellulose; sodium alginate and gum arabic, for example. Also, the present compositions may further contain cosmetically acceptable dyes or pigments which may have the effect of rein-forcing hair colors or varying the color of the instant shampoos.

The following example is given to further illustrate the present invention. All relative proportions are set forth as percentages by weight.

EXAMPLE

A hair treatment composition in the form of a shampoo is prepared according to the invention as described hereinabove by mixing the following ingredients:

| INGREDIENT | WT. PERCENT |
| --- | --- |
| Liquid castile soap | 50.0 |
| Extract from corncobs | 28.0 |
| Aloe vera gel | 22.0 |

The above shampoo composition has been found to be effective in treating a wide variety of scalp affections. When topically applied daily or several times a week to the hair and scalp in the conventional manner for a period of at least several weeks, the above shampoo positively prevented generation of dandruff and itching on the scalp in a number of reported cases. Also, a noticeable increase in luster and body, as well as an improvement in the overall cosmetic properties of the hair was observed.

In addition, the application of the instant composition to the hairless portion and thinning section of the scalp of a elderly male resulted in the observation of new hair growth from the pores of the hairless section and thickening of the hair in the thinning section. The hair growth effect of the active ingredients used in the present invention is not clearly understood and no scientific theory is proposed herein. However, the lack of an attempted explanation for the hair-growing results and therapeutic effects of the instant shampoo should be held without prejudice to the present invention.

It should be understood that there may be various changes and modifications of the representative embodiments herein chosen for purposes of illustration without departing from the spirit and scope of the invention. Accordingly, the foregoing description and illustration are not to be interpreted as restrictive of the invention beyond that necessitated by the following claims.

I claim:

1. A therapeutic shampoo composition for the treatment of scalp affections consisting essentially of about 45-55% by weight of liquid castile soap, about 25-30% by weight of a corncob extract and 20-25% by weight of aloe vera gel.

2. The composition of claim 1 wherein the liquid castile soap is an aqueous solution having a concentration of about 5-10% by weight of castile soap.

3. The composition of claim 2 wherein the liquid castile soap is prepared by dissolving dry castile soap in water to obtain a soap solution, boiling said soap solution until a paste is formed, and diluting said paste with sufficient water to prepare said aqueous soap solution.

4. The composition of claim 1 wherein the corncob extract is an aqueous concentrate containing about 20% by weight of insoluble constituents of corncob.

5. The composition of claim 4 wherein the corncob extract is prepared by drying corncobs, reducing the dried corncobs by grounding, and extracting the ground corncobs with water by cooking a mixture of the ground corncobs and water until said aqueous concentrate results.

6. A method for suppressing the generation of dandruff and itching of the scalp which comprises applying to the hair or scalp a therapeutically effective amount of the shampoo composition according to claim 1.

* * * * *